United States Patent [19]
Polson et al.

[11] Patent Number: 6,017,936
[45] Date of Patent: Jan. 25, 2000

[54] METHOD FOR PRODUCING PARTICLES OF PYRITHIONE SALTS AND PARTICLES SO PRODUCED

[75] Inventors: George A. Polson, Harwinton; Richard H. Dumas, East Haven; Rahim Hani, Cheshire, all of Conn.

[73] Assignee: Arch Chemicals, Inc., Norwalk, Conn.

[21] Appl. No.: 09/032,959

[22] Filed: Mar. 2, 1998

Related U.S. Application Data

[60] Provisional application No. 60/040,793, Mar. 14, 1997.

[51] Int. Cl.$^7$ .............................. A61K 31/44; C07F 9/80; C07D 211/72; C07D 211/84; C07D 213/63
[52] U.S. Cl. ................................ 514/345; 546/6; 546/290
[58] Field of Search ......................... 546/6, 290; 514/345

[56] References Cited

U.S. PATENT DOCUMENTS

| | | | |
|---|---|---|---|
| 2,786,847 | 3/1957 | Cislak | 260/294.8 |
| 2,809,971 | 10/1957 | Bernstein et al. | 260/270 |
| 3,589,999 | 6/1971 | McRae et al. | 210/28 |
| 3,590,035 | 6/1971 | Damico | 260/290 |
| 3,773,770 | 11/1973 | Damico | 260/290 |
| 4,323,683 | 4/1982 | Bolich et al. | 546/6 |
| 4,345,080 | 8/1982 | Bolich et al. | 546/6 |
| 4,632,991 | 12/1986 | Maurer et al. | 546/6 |
| 4,659,830 | 4/1987 | Maurer et al. | 546/6 |
| 4,670,430 | 6/1987 | Imamura et al. | 514/188 |
| 4,940,578 | 7/1990 | Yoshihara et al. | 424/70 |
| 5,104,645 | 4/1992 | Cardin et al. | 424/70 |
| 5,230,833 | 7/1993 | Romberger et al. | 252/363.5 |
| 5,246,489 | 9/1993 | Farmer, Jr. et al. | 106/18.33 |
| 5,540,860 | 7/1996 | Hosseini et al. | 252/308 |
| 5,614,538 | 3/1997 | Nelson | 514/345 |
| 5,650,095 | 7/1997 | Hosseini et al. | 252/308 |
| 5,675,013 | 10/1997 | Hani et al. | 514/348 |
| 5,696,083 | 12/1997 | Nelson | 514/845 |
| 5,723,110 | 3/1998 | Yamamoto et al. | 424/65 |

*Primary Examiner*—Alan L. Rotman
*Assistant Examiner*—Rita Desai
*Attorney, Agent, or Firm*—Todd E. Garabedian; Dale L. Carlson; Wiggin & Dana

[57] ABSTRACT

The present invention relates to a method for producing submicron-sized particles of pyrithione salts, comprising reacting pyrithione or a water-soluble salt of pyrithione and a water-soluble polyvalent metal salt in a pressurized turbulent flow reactor that generates pulverizing forces, the reaction producing submicron sized particles of pyrithione salt. The present invention also relates to particles made by the above method, and products, such as shampoos, soaps, and skin care medicaments made using these particles.

27 Claims, No Drawings

METHOD FOR PRODUCING PARTICLES OF PYRITHIONE SALTS AND PARTICLES SO PRODUCED

CROSS-REFERENCE TO RELATED APPLICATION

This application claims the benefit of provisional patent Application Serial No. 60/040,793, filed Mar. 14, 1997.

BACKGROUND OF THE INVENTION

1. Field of the Invention

The present invention relates generally to a method for preparing particles of pyrithione salts, and more specifically to a method of preparing submicron-sized particles of pyrithione salts under pressurized, turbulent conditions. The present invention also relates to particles made by the method, as well as products made with the particles produced by the method.

2. Description of the Related Art

Polyvalent metal salts of pyrithione (also known as 1-hydroxy-2-pyridinethione; 2-pyridinethiol-1-oxide; 2-pyridinethione; 2-mercaptopyridine-N-oxide; pyridinethione; and pyridinethione-N-oxide) are known to be effective biocidal agents, and are widely used as fungicides and bactericides in paints and personal care products such as anti-dandruff shampoos. The polyvalent metal salts of pyrithione are only sparingly soluble in water and include magnesium pyrithione, barium pyrithione, strontium pyrithione, copper pyrithione, zinc pyrithione, cadmium pyrithione, and zirconium pyrithione. The most widely used divalent pyrithione salts are zinc pyrithione and copper pyrithione.

Zinc and copper pyrithione are useful as antimicrobial agents active against gram-positive and negative bacteria, fungi, and yeasts. Zinc pyrithione is used as an antidandruff component in shampoos, while technical suspensions of zinc pyrithione and/or copper pyrithione are used as preservatives and antifouling agents in paints and polymers. Synthesis of polyvalent pyrithione salts are described in U.S. Pat. No. 2,809,971 to Berstein et al. Other patents disclosing similar compounds and processes for making them include U.S. Pat. Nos. 2,786,847; 3,589,999; 3,590,035; 3,773,770.

Known methods for producing insoluble polyvalent salts of pyrithione result in large solid particles having an average size greater than 2 micrometers ($\mu$m). However, smaller particles of pyrithione salts (i.e., less than 1 micrometer or submicron) are often desired because they more easily form suspensions and provide a larger surface area for enhanced biocidal activity. In addition, smaller particles, particularly in the low submicron range (e.g., below about 0.2 $\mu$m), are transparent to light, and thus provide the opportunity to manufacture "clear" products, such as clear shampoos and soaps, that are popular in the marketplace today.

Smaller particles of pyrithione salts are usually generated by a separate mechanical manipulation step (e.g., grinding or crushing) on larger particles or crystals that are made by conventional processes. For example, European Patent Application No. 70046 describes preparation of zinc pyrithione using organic solvents. This process results in production of large crystals of zinc pyrithione that are easily isolated by filtration. A separate, optional grinding step is used to grind the large crystals and produce zinc pyrithione particles of smaller size.

As another example, U.S. Pat. No. 4,670,430 describes a process of making zinc pyrithione particles with a median size of about 0.2 $\mu$m by grinding larger zinc pyrithione particles.

There is currently no single step method for producing particles of pyrithione salts in the submicron size range. The separate step of grinding larger particles to produce smaller particles, as described in the prior art, generally results in substantial loss of useful product, and is costly in terms of equipment, time, and energy required. Accordingly, what is needed in the art is a method to prepare pyrithione salt particles in the submicron size range without a separate mechanical crushing or grinding step. The present invention is believed to be an answer to that need.

SUMMARY OF THE INVENTION

In one aspect, the present invention relates to a method for producing submicron-sized particles of pyrithione salts, comprising reacting pyrithione or a water-soluble salt of pyrithione and a water-soluble polyvalent metal salt in a pressurized turbulent flow reactor that generates pulverizing forces, the reaction producing submicron sized particles of pyrithione salt.

In another aspect, the present invention relates to a method for producing submicron-sized particles of zinc pyrithione comprising reacting a pyrithione or a water-soluble salt of pyrithione and a water-soluble zinc salt selected from the group consisting of zinc sulfate, zinc chloride, zinc acetate, and combinations thereof, in a turbulent flow reactor generating pulverizing forces, the turbulent flow reactor maintained at a pressure of from about 18,000 psi to about 23,000 psi and a temperature of from about 0° C. to about 23° C., the reaction producing submicron-sized particles of zinc pyrithione.

In yet another aspect, the present invention relates to particles produced by the above methods, and products made using particles made by the method of the invention.

These and other aspects will become apparent upon reading the following detailed description of the invention.

DETAILED DESCRIPTION OF THE INVENTION

It now has been surprisingly found, in accordance with the present invention, that a solution is provided to the problem of efficiently producing pyrithione salt particles of submicron size in a single operation. The present inventors have solved this problem by reacting pyrithione or a water-soluble salt of pyrithione, and a water-soluble polyvalent metal salt in a pressurized, turbulent flow reactor that generates pulverizing forces. The pulverizing forces produced by the pressurized, turbulent flow reactor efficiently generate pyrithione salt particles of submicron size without resorting to a separate mechanical grinding or crushing step. The submicron-sized pyrithione salt particles made by the method of the invention have a narrow and uniform size distribution, and have excellent surface deposition properties due to the large surface area provided by the population of submicron particles. This large surface area results in improved biocidal efficacy in shampoos, soaps and paints. In addition, the submicron-sized particles made according to the method of the invention more easily form suspensions when combined with other compounds, and the suspensions thus formed have greater physical stability against settling of the particles.

As used herein, the term "water-soluble salts of pyrithione" or "water-soluble pyrithione salts" include those salts of pyrithione in which the hydrogen atom of the thiol group is substituted with a monovalent cation. The term "water-soluble polyvalent metal salt" refers to those salts in which the cation has a charge of +2 or greater. The terms "elevated pressure" and/or "pressurized" are defined herein as any pressure greater than about 1 atm. The terms "turbulent" and "turbulence" refer to departure in a fluid from a smooth flow where the velocity of the fluid at a given point varies erratically in magnitude and direction. The term "flow reactor" refers to a device which manipulates a fluid stream containing reactants, products, reaction medium, or a combination thereof. The term "pulverizing forces" is defined herein as those forces which affect particle size reduction under turbulent flow conditions, such as shear forces, impact forces, cavitation forces, sonication forces, or combinations of these. The term "submicron" is defined herein as any size less than 1 micrometer ($\mu$m). Preferred ranges of submicron particles are from about 0.01 $\mu$m to about 0.99 $\mu$m. The terms "particles of pyrithione salts" and "pyrithione salt particles" as used herein refer to those salts of pyrithione that form precipitates and are essentially insoluble or sparingly soluble in the surrounding medium.

In accordance with the process of the present invention, pyrithione or a water-soluble salt of pyrithione is reacted with a water-soluble salt of a selected polyvalent metal in a pressurized turbulent flow reactor that generates pulverizing forces. The pulverizing forces generated under the pressure and turbulence of the flow reactor efficiently reduce the pyrithione salt particles produced by the reaction to submicron size as they are formed. Pyrithione in its acid form, or a water-soluble salt of pyrithione may be used in the reaction. Useful water soluble salts of pyrithione preferably include an ammonium ion or an alkali metal ion. Accordingly, exemplary water soluble salts of pyrithione include sodium pyrithione, potassium pyrithione, lithium pyrithione, ammonium pyrithione, and combinations thereof. The most preferred water-soluble salt of pyrithione in the present invention is the sodium salt (i.e., sodium pyrithione). The amount of pyrithione or water-soluble salt of pyrithione can vary over a wide range, and establishing a useful amount is understood to be within the capabilities of the ordinary skilled practitioner based on the stoichiometry of the reaction and the required amount of submicron particles of pyrithione salt that must be generated. A preferred amount of pyrithione or water-soluble pyrithione salt is from about 3% to about 52% by weight of the total weight of the reaction mixture.

Exemplary water-soluble polyvalent metal salts useful in accordance with the method of the invention include zinc salts, tin salts, cadmium salts, copper salts, zirconium salts, magnesium salts, aluminum salts, and the like. Combinations of these salts may also be employed. Useful counterions for these metals include nitrates, acetates, sulfates, halides or combinations thereof. Preferred water-soluble polyvalent metal salts include zinc chloride ($ZnCl_2$), copper chloride ($CuCl_2$), zinc acetate ($ZnO_2CCH_3$) and zinc sulfate ($ZnSO_4$). The amount of water-soluble polyvalent metal salt may vary depending on the amount of pyrithione or water-soluble salt of pyrithione used in the reaction. The molar ratio of pyrithione or water-soluble salt of pyrithione to the water-soluble polyvalent metal salt is generally in the range from about 1:2 to about 1:8. Preferably, a slight stoichiometric excess (e.g., 5% of water-soluble polyvalent metal salt by weight over pyrithione or water-soluble salt of pyrithione) is desirable to ensure a complete reaction.

Useful media for the reaction include aqueous media such as water, or water in combination with one or more organic solvent(s). Useful organic solvents include alcohols, such as methanol, ethanol, amines such as diethanolamine, ether, esters, and the like.

Additional materials, such as dispersants may be added to the reactants during the precipitation reaction to prevent agglomeration of the pyrithione salt particles. Alternatively, the dispersant may be added at the completion of the reaction to prevent particle agglomeration. Preferably, the dispersant is a salt of polymerized alkyl naphthalene sulfonic acid, such as "DARVAN 1" (sodium naphthalene sulfonic acid formaldehyde, a product of R. T. Vanderbilt Co. Inc.), "DEMOL N" (sodium salt of naphthalene sulfonic acid, a product of Kao Chemicals), "DAXAD 11" (sodium salt of polymerized alkyl naphthalene sulfonic acids, a product of W. R. Grace & Co.), "TAMOL N" (sodium salt of condensed naphthalene sulfonic acid, a product of Rohm and Haas Co.), "HAROL KG" (potassium salts of polymerized alkyl naphthalene sulfonic acids, a product of Graden Chemical Co.), "HAROL RG-71" (sodium salts of polymerized alkyl naphthalene sulfonic acids, a product of Graden Chemical Co.), "LOMAR LS" (sodium salt of condensed mononaphthalene sulfonic acid, a product of Henkel Corp.) and the like. Additional useful dispersants are disclosed in McCutcheons Handbook of Functional Materials (North American Volume I, 1992, pp 117–137) which is incorporated by reference in its entirety herein. Combinations of two, three, four, or more dispersants as described herein may also be used according to the invention.

The dispersants employed in the method of the present invention may suitably be combined with a surfactant. Useful surfactants may be selected from the classes of surfactants known as nonionics, anionics, cationics, and amphoterics (the latter being also commonly referred to as "zwitterionics") . The surfactants are suitably employed singly, or in combinations of two, three, or even four or more surfactants selected from the above-mentioned four classes.

Useful nonionic surfactants include linear alcohol alkoxylates, such as the linear alcohol ethoxylates, ethoxylated/propoxylated block copolymers, ethoxylated/propoxylated fatty alcohols, and polyoxyethylene cetyl ethers, and the like. Useful linear alcohol alkoxylates are commercially available, for example, under the registered trademark POLY-TERGENT SL-42, a product of Olin Corporation. If desired, the alcohol alkoxylate is suitably end-capped with a lower alkyl group, and such a product is commercially available as POLY-TERGENT SLF-18, a propylene oxide-capped linear alcohol alkoxylate that is also a product of Olin Corporation, and these end-capped linear alcohol alkoxylates are notably low foaming during use. Also advantageous for use in accordance with the present invention are surfactants within the group commercially available as POLY-TERGENT SLF-18B series surfactants, which are surfactants characterized by enhanced biodegradability (also products of Olin Corporation), being alkene oxide-capped linear alcohol alkoxylates, containing ethylene oxide moieties in the backbone, and suitably also containing at least one propylene oxide moiety in the backbone, as disclosed, for example, in U.S. Pat. Nos. 4,925,587 and 4,898,621.

Other useful nonionic surfactants include one commercially available as NEODOL 91-6, a registered trademark surfactant product of Shell Chemical. This surfactant is a detergent range mixture of $C_9$–$C_{11}$ linear primary alcohol ethoxylates having an average of six moles of ethylene oxide per mole of alcohol. Other useful nonionic surfactants include those containing a linear $C_9$–$C_{11}$ carbon chain and five or six ethylene oxide or propylene oxide groups per molecule.

Useful anionic surfactants include alkyl diphenylether disulfonates, alkyl phenyl ethoxylated phosphate esters, carboxylated linear alcohol alkoxylates, linear alkyl benzene sulfonic acid, diisobutyl sulfosuccinate, and alkyl sulfonates. Useful anionics also include the alkylated diphenyl oxide sulfonates, and their methods of preparation are well-known, as illustrated by the disclosures of U.S. Pat. Nos. 3,264,242; 3,634,272; and 3,945,437, the disclosures of which are all incorporated herein by reference. Commercial methods of preparation of the alkylated diphenyl oxide sulfonates generally do not produce species which are monoalkylated, monosulfonated, dialkylated or disulfonated. The commercially available species typically are predominately (greater than 90 percent) disulfonated and are a mixture of mono- and di-alkylated with the percentage of dialkylation being about 15 to about 25 percent, and the percentage of monoalkylation being about 75 to 85 percent. Most typically, the commercially available species are about 80 percent monoalkylated and 20 percent dialkylated.

Two illustrative commercially available solutions containing alkylated diphenyl oxide sulfonate surfactants are DOWFAX 8390 and DOWFAX 8390A surfactants, trademarked products of The Dow Chemical Company. In each, the alkyl group is predominantly a hexadecyl $C_{16}$ group. These products are suitably employed in a solution fully or partially neutralized with ammonium hydroxide if desired.

An advantageous anionic surfactant is also provided by reacting the above-described alkylated diphenyl oxide sulfonates with a piperazine compound to produce a molar ratio of sulfonate compound to piperazine compound of between about 10:1 and about 1:10, preferably between about 2:1 and about 1:2. Although any piperazine compound can be used for such reaction, preferred compounds include those selected from the group consisting of 1,2-aminoethyl piperazine, 1,4-piperazinediethane sulfonic acid, anhydrous piperazine, hydrated piperazine, and combinations thereof.

Other useful anionics are polycarboxylated alcohol alkoxylates, preferably those selected from acids or organic or inorganic salts of the following: polycarboxylated linear alcohol alkoxylates, polycarboxylated branched alcohol alkoxylates, polycarboxylated cyclic alcohol alkoxylates, and combinations thereof. These polycarboxylated alcohol alkoxylates typically contain at least two succinic acid radicals per molecule. Preferred polycarboxylated alcohol alkoxylates are those having a backbone containing both poly(propylene oxide) and poly(ethylene oxide) blocks, and such preferred polycarboxylated alcohol alkoxylates are readily commercially available, for example, as POLY-TERGENT CS-1, a trademarked surfactant of Olin Corporation. If desired, at least a portion of the acid groups on the polycarboxylated alcohol alkoxylate are neutralized with a base to provide the corresponding salt. Suitable bases include alkali metal hydroxides, alkaline earth metal hydroxides, and metal-free hydroxides, including potassium hydroxide, ammonium hydroxide, calcium hydroxide, magnesium hydroxide, ammonia, mono-, di- and tri-ethanol amines, and combinations thereof. Sodium hydroxide is preferred, and although potassium hydroxide can be employed, it is not preferred. The organic or inorganic base is preferably employed in at least an equimolar amount relative to the number of moles of polycarboxylated alcohol alkoxylated used. The polycarboxylated alcohol may also contain a polycarboxylic acid, for example, polyacrylic acid, along with the starting alcohol alkoxylate and esters of the alkoxylate of the polycarboxylic acid.

Although individually the cationic and the amphoteric surfactants are acceptable for use in the process of the present invention, they may also be used in combination with at least one surfactant from one of the other classes. Illustrative cationics include alkyl triammonium halide, non-linear alkyl dimethyl halide and alkyl dimethyl benzyl ammonium halide-containing surfactants. Illustrative amphoteric surfactants include polyglycol ether derivatives, ethoxylate oxazoline derivatives, lauramidopropyl betaine, and lecithin.

Suitable blends can be employed in the process of the present invention based on various combinations of the above-described surfactants. Such a blend can be any combination of two or more surfactants, between or within the above-described four broad classes of surfactants. Combinations can include blends of: anionic with anionic, anionic with nonionic, anionic with cationic, anionic with amphoteric, cationic with cationic, cationic with amphoteric, nonionic with nonionic, nonionic with amphoteric, and amphoteric with amphoteric. Likewise, ternary and quaternary blends of surfactants by selecting three or four surfactants, respectively, from within or among the above-described classes.

Suitably, any single or combination of two, three or four surfactants from the following illustrative list are suitably employed: (a) nonionics, including alkoxylated linear alcohols (such as POLY-TERGENT SLF-18 surfactant, a product of Olin Corporation), linear alcohol ethoxylates (such as NEODOL 91-8 surfactant, a product of the Shell Corporation), ethoxylated linear alkyl benzene (such as TRITON X-100 surfactant, a product of Union Carbide Corporation), and EO/PO block copolymers (such as POLY-TERGENT E-17A surfactant, a product of Olin Corporation); (b) anionics, including alkyl diphenyl ether disulfonates (such as POLY-TERGENT 2A1 surfactant, a product of Olin Corporation), alkyl phenyl ethoxylated phosphate esters (such as Wayfos M-60 surfactant, a product of Olin Corporation), carboxylated linear alcohol alkoxylates (such as POLY-TERGENT CS-1 surfactant, a product of Olin Corporation), linear alkyl benzene sulfonic acid (such as BIOSOFT S-130 surfactant, a product of Stepan Company), alpha-olefin sulfonates (such as BIO TERG AS-40 surfactant, a product of Stepan Company), dialkyl-sulfosuccinates (such as AROWET SC-75 surfactant, a product of Arol Chemical Products), and alkyl sulfates (such as STEPANOL SLS surfactant, a product of Stepan Company); (c) cationics including alkyl triammonium halides (such as CTAB surfactant, a product of VWR Scientific Inc.), polyoxyethylene cocoamine (such as MAZEEN surfactant, a product of PPG Industries), primary alkyl amines (such as ARMEEN surfactant, a product of Akzo Chemical Co.), dicoco dimethyl ammonium halide (such as JET QUAT surfactant, a product of Jetco Chemical Inc.), di-isodecyl dimethyl ammonium halides (such as AMMONYX K9 surfactant, a product of Stepan Company), and diethyl aminoethyl stearate (such as CERASYNT 303 surfactant, a product of ISP Van Dyke); and, (d) amphoterics, including polyglycol ether derivatives (such as ALBEGAL A surfactant, a product of Ciba-Geigy), ethoxylated oxazolin derivatives (such as ALKATERG T-IV surfactant, a product of Angus Chemicals), lauramide propyl betain (such as LEXAINE C surfactant, a product of Inolex Chemicals), lecithin (such as CANASPERSE surfactant, a product of Can Amoral), disodium cocoamphodiacetate (such as MONATERICS surfactant, a product of Mona Industries), complex fatty amine salt (such as MAFO 13 surfactant, a product of PPG Industries), and cocoamine oxide (such as MACKAMINE CO surfactant, a product of the McIntyre Group Ltd.).

The dispersant or dispersant/surfactant combination is preferably employed in a total amount of between about 0.05 and 10%, more preferably between about 0.1 and 5%, most preferably between about 0.5 and about 1.5% by weight, based on the total weight of the reaction mixture.

In order to efficiently produce submicron-sized particles of pyrithione salt, the reactants are reacted in a flow reactor under conditions of high pressure and turbulence. The combination of high pressure and turbulence generates pulverizing forces within the flow reactor and affects size reduction of the pyrithione salt particles simultaneously as they are formed in the reaction. In a preferred embodiment, sodium pyrithione is reacted with zinc chloride, zinc sulfate, zinc acetate, or a combination thereof in a flow reactor that generates pulverizing forces (e.g., Model M-140K Laboratory Microfluidizer Processor available from Microfluidics International Corp., Newton Mass.). The reaction products are submicron-sized particles of zinc pyrithione, along with aqueous sodium chloride, aqueous sodium sulfate, or aqueous sodium acetate as by-products.

Pressure may be generated in the flow reactor by any method known in the art, such as by pump, piston, and the like. In one embodiment, the reactants are pumped under high pressure into a mixing chamber via air-powered pumps. The high pressure capabilities of the pumps result in generation of pressures on the reactants as high as about 50,000 psi. Preferably, pressures useful in the reaction are in the range of 10,000 to 50,000 psi, more preferably in the range of 18,000 to 23,000, and most preferably in the range of 18,000 to 20,000 psi.

Turbulence may be generated in the flow reactor by perturbing the pressurized laminar flow of the reaction mixture as it passes through the flow reactor. Turbulence may be generated by any means known in the art. However, the pressurized laminar flow of the reaction mixture must be perturbed to an extent sufficient to generate pulverizing forces that affect size reduction of the pyrithione salt particles. In one embodiment, baffles may be placed in the flow reactor to perturb the laminar flow of reactants as they move through the flow reactor under high pressure. In another embodiment, the pressurized reaction mixture (which may include pyrithione salt particles and aqueous by-products) is passed through a fixed geometry interaction chamber where it is divided into a plurality of streams, for example two streams. The streams are then brought together such that the high pressure and turbulent forces of stream convergence result in overall particle size reduction by generation of pulverizing forces. The size reducing forces generated by stream convergence include, for example, shear forces, impact forces, cavitation forces, and the like, or combinations of these, and result in effective size reduction of the particles.

The interaction chamber apparatus may be used in a "single-pass" mode to subject newly-generated pyrithione salt particles to size reduction forces only once. Alternatively, the pyrithione salt particles may be repeatedly subjected to the forces generated in the interaction chamber by repeatedly dividing and reconverging the reaction mixture in a "multiple-pass" mode. The interaction chamber may be fitted with cooling or heating coils to maintain a desired temperature.

In general, higher pressures produce smaller particles in accordance with the method of the invention. As an example, pressures of about 10,000 psi produce particles in the range of about 0.7 to 0.95 μm. Pressures of about 18,000 psi generally produce particles in the range of about 0.3 to 0.4 μm. Accordingly, one skilled in the art can easily modify the pressures to attain populations of desired particle sizes.

The temperature of the reaction and flow reactor may be maintained at any temperature which permits precipitation of pyrithione salt. Generally, lower temperatures promote the formation of smaller particles; therefore, lower temperatures are preferred. Accordingly, the reaction temperature is preferably between the freezing point of the aqueous medium and ambient temperature (about 23° C.), more preferably between about 0 and about 15° C., and most preferably between about 0° C. and about 7° C. A particularly useful temperature range is from about 5 to about 7° C.

The particles of insoluble pyrithione salt made by the method of the invention have a narrow submicron size range, preferably in the range of about 0.03 μm to about 0.95 μm, more preferably in the range of about 0.04 μm to about 0.88 μm, and most preferably in the range of about 0.30 μm to about 0.45 μm. The pyrithione salt particles may be isolated from the by-products by filtration or other isolation methods known in the art. Alternatively, the mixture of particles and by-products may be added to commercial products directly without further purification. The by-products (e.g., aqueous sodium chloride, aqueous sodium sulfate, or aqueous sodium acetate) are useful in shampoo or soap formulations as thickeners. Addition of the combination of pyrithione salt particles and by-products made in accordance with the present invention is efficient from a manufacturing standpoint due to the large cost savings in eliminating separation, isolation and purification steps.

The particles produced according to the method of the invention are useful as additives in a variety of items such as personal care products (soaps, shampoos, and the like), paints, coatings, fertilizers, and foodstuffs. For example, zinc pyrithione particles made according to the method of the invention are a useful antidandruff additive to antidandruff shampoos.

EXAMPLES

The following examples are intended to illustrate, but in no way limit the scope of the present invention. All parts and percentages are by weight and all temperatures are in degrees Celsius unless explicitly stated otherwise. In the following Examples "q.s." means quantity sufficient, generally 0.1 to 2% by weight.

Example 1

Production of Submicron Particles of Zinc Pyrithione

A solution of 24 g of 20% $ZnSO_4$, 0.5 g "DARVAN" (sodium salt of polymerized alkyl naphthalene sulfonic acids) and 25.5 g of water is introduced into and recirculated through a model M-140K Laboratory Microfluidizer Processor (Microfluidics International Corp., Newton Mass.) which included a fixed geometry interaction chamber. The entire apparatus is cooled to approximately 7° C., and pressure is maintained in the Microfluidizer at about 18,000 psi. A solution of sodium pyrithione (45 mL of a 16.3% solution) is added to the inlet of the reservoir of the Microfluidizer over an 8 minute period, and circulation of the reactants continued for 5–10 minutes. As the reaction mixture circulated through the Microfluidizer apparatus, the fixed geometry interaction chamber divides the reaction mixture into two streams. The streams are then brought together under pressure to generate turbulence and pulverizing forces that result in size reduction of the zinc pyrithione particles. The particles of zinc pyrithione thus formed are measured by a laser light scattering particle size analyzer (Horiba LA910). Table I shows the size distribution and frequency of the particles. The median particle size is approximately 0.313 μm. The particle size distribution is very narrowly dispersed (nearly mono dispersed) and exhibits a size range from about 0.30 to about 0.45 μm.

TABLE I

| Size(μm) | Frequency (%) | Cumulative (%) |
|---|---|---|
| 0.445 | 0.25 | 100.0 |
| 0.389 | 22.41 | 99.75 |
| 3.39 | 64.35 | 77.34 |
| 0.296 | 13.00 | 13.00 |

Example 2

Production of Submicron Particles of Copper Pyrithione

In a manner similar to Example 1, 100 mL of a 3% aqueous solution of sodium pyrithione is introduced into and recirculated through a Microfluidizer apparatus maintained at about 20,000 psi and at approximately 5° C. 50 mL of a 2.42% $CuCl_2$ solution is added to this circulating solution which is maintained at 5° C. The size and distribution of particles of copper pyrithione generated from one pass through the Microfluidizer is measured using a Horiba LA910 laser. Analysis revealed that the particle sizes ranged from 0.04 to 0.88 μm, with a median size of about 0.09 μm.

Example 3

(Proposed Example) Antidandruff Shampoo Formulation I

An antidandruff shampoo composition is made using the zinc pyrithione particles made as described in Examples 1 and 2 in combination with the following ingredients:

| Component A: | |
|---|---|
| Water | 41.0% |
| Magnesium aluminum silicate | 1.0% |
| Hydroxypropyl methylcellulose | 0.8% |
| Component B: | |
| Zinc Pyrithione (needles/rods, 25% aqueous dispersion) | 4.0% |
| Component C: | |
| Cocamide DEA | 1.0% |
| Component D: | |
| Triethanolamine lauryl sulfate, 40% | 40.0% |
| Triethanolamine, 99% | 3.2% |
| FD&C Blue No. 1 (0.2%) | 1.5% |
| FD&C Yellow No. 5 (0.1%) | 0.5% |
| Fragrance | q.s. |

The antidandruff shampoo composition was made as follows:

Component A is prepared by heating water to 70° C. and dissolving the other two components with stirring (about 1500 rpm). The temperature of the mixture is lowered to 50° C., and Component B is added, and stirring continued for 5 minutes. Stirring speed is reduced to ~300 RPM. Component C is melted in a separate container, and added to the A/B mixture. The heat is removed and component D is added while the mixture cools.

Example 4

(Proposed Example) Antidandruff Shampoo Formulation II

Another antidandruff shampoo composition is made using the zinc pyrithione particles made as described in Examples 1 and 2 in combination with the following ingredients:

| Component A: | |
|---|---|
| Deionized water | 76.0% |
| Ammonium lauryl sulfate | 15.0% |
| Cocamide DEA | 2.0% |
| Component B: | |
| Di(hydrogenated) tallow phthalic acid amide | 5.0% |
| Zinc Pyrithione (needles/rods, 25% aqueous dispersion) | 4.0% |
| Component C: | |
| Preservative | q.s. |
| Component D: | |
| Citric Acid, 50% aq. Solution, OR Sodium hydroxide, 50% aqueous solution | q.s. |
| Component E: | |
| Ammonium chloride | q.s. |

The antidandruff shampoo composition is made as follows:

In separate containers, components A and B are each mixed well. Component A is heated to 60° C. and component B is added. The mixture is stirred for 30 minutes. The mixture is then cooled to 50° C., and component C is added. The pH of the resulting mixture is adjusted to 5.0–6.2 with component D, and the viscosity is adjusted with component E.

Example 5

(Proposed Example) Antidandruff Shampoo with Conditioner I

An antidandruff shampoo and conditioner composition is made using the zinc pyrithione particles made as described in Examples 1 and 2 in combination with the following ingredients:

| Component A: | |
|---|---|
| Deionized Water | 77.0% |
| Ammonium lauryl sulfate | 20.0% |
| Cocamide DEA | 2.0% |
| Component B: | |
| Di(hydrogenated) tallow phthalic acid amide | 4.0% |
| Zinc Pyrithione (needles/rods, 25% aqueous dispersion) | 4.0% |
| Dimethicone, 12,000 cps | 0.5% |
| Component C: | |
| Preservative | q.s. |
| Component D: | |
| Citric acid, 50% aqueous solution, OR Sodium hydroxide, 50% aqueous solution | q.s. |
| Component E: | |
| Ammonium chloride | q.s. |

The antidandruff shampoo and conditioner composition is made as follows:

In separate containers, components A and B are each mixed well. Component A is heated to 60° C. and component B is added. The mixture is stirred for 30 minutes. The mixture is then cooled to 50° C., and component C is added.

The pH of the resulting mixture is adjusted to 5.0–6.2 with component D, and the viscosity is adjusted with component E.

Example 6

(Proposed Example) Antidandruff Shampoo with Conditioner II

Another antidandruff shampoo and conditioner composition is made using the zinc pyrithione particles made as described in Examples 1 and 2 in combination with the following ingredients:

| Component A: | |
| --- | --- |
| Deionized water | 21.75% |
| Guar hydroxypropyl trimonium chloride | 0.30% |
| Magnesium Aluminum Silicate | 0.70% |
| Zinc Pyrithione (needles/rods, 25% aqueous dispersion) | 4.0% |
| Component B: | |
| Sodium laureth sulfate | 30.0% |
| Ammonium xylene sulfonate, 40% aq. | 02.0% |
| Component C: | |
| Tricetylammonium chloride | 0.50% |
| Cetyl alcohol NF | 0.40% |
| Stearyl alcohol | 0.40% |
| Glycol distearate | 2.00% |
| Component D: | |
| Cocamide MEA | 1.70% |
| Ammonium lauryl sulfate | 36.00% |
| Component E: | |
| Preservative | 0.05% |
| Fragrance and dye | q.s. |
| Component F | |
| Citric acid, 25% aqueous solution | q.s. |

The antidandruff shampoo and conditioner composition is made as follows:

Component A is prepared by heating water to 50° C. and dispersing the guar hydroxypropyl trimonium chloride and the magnesium aluminum silicate with rapid agitation. The zinc pyrithione dispersion is added to this combination with stirring. The pH of component A is adjusted to 4.5–5.0 with component F. Both components of B are slowly added to component A, mixing well. The pH of the mixture is adjusted to 5.7–6.3 with component F. In a separate container, component C is heated to 70–75° C. The A/B mixture is heated to 60° C. and blended with component C, mixing well. Both components of D are added to the hot mixture, and stirred well. The pH of the mixture is adjusted to 5.7–6.3 with component F. The mixture is cooled to 40–45° C., and component E is added with stirring. If desired, the viscosity of the product can be increased by adding 0.05–1% sodium chloride.

Example 7

(Proposed Example) "Extra Body" Antidandruff Shampoo

An "extra body" antidandruff shampoo and conditioner composition is made using the zinc pyrithione particles made as described in Examples 1 and 2 in combination with the following ingredients:

| Component A: | |
| --- | --- |
| Deionized Water | 62.6% |
| Zinc Pyrithione (needles/rods, 25% aqueous dispersion) | 4.0% |
| Component B: | |
| Methyl Paraben | 0.30% |
| Propyl Paraben | 0.10% |
| Propylene Glycol | 0.50% |
| Sodium Chloride | 0.50% |
| Component C: | |
| Triethanolamine lauryl sulfate | 20.0% |
| Cocamide MEA | 4.0% |
| Ethylene glycol distearate | 7.0% |
| Component D: | |
| Cocodimonium hydrolyzed animal protein | 1.00% |
| Component E: | |
| FD&C Blue No. 1 | q.s. |
| Component F: | |
| Citric Acid, 50% aqueous solution | q.s. |

The antidandruff shampoo and conditioner composition is made as follows:

Component A is heated to 60° C. The ingredients of component B are added with good stirring until dissolved. The ingredients of component C are added to the mixture sequentially, and heated with mixing at 60° C. The mixture is cooled with stirring to 40° C., and components D and E are added with stirring. The pH of the final composition is adjusted to 4.7 with component F.

Although the invention has been shown and described with respect to illustrative embodiments thereof, it should be appreciated that the foregoing and various other changes, omissions and additions in the form and detail thereof may be made without departing from the spirit and scope of the invention as delineated in the claims. All patents and patent applications mentioned are herein incorporated by reference in their entirety.

What is claimed is:

1. A method for producing submicron-sized particles of pyrithione salts having sizes from about 0.01 $\mu$m to about 0.99 $\mu$m, comprising reacting pyrithione or a water-soluble salt of pyrithione and a water-soluble polyvalent metal salt selected from the group consisting of zinc salts, tin salts, cadmium salts, bismuth salts, copper salts, zirconium salts, magnesium salts, aluminum salts, nitrate salts, acetate salts, sulfate salts, halide salts, and combinations thereof, in a pressurized turbulent flow reactor that generates pulverizing forces, said reaction producing said submicron sized particles of pyrithione salt.

2. A method for producing submicron-sized particles of pyrithione salts having sizes from about 0.01 $\mu$m to about 0.99 $\mu$m, comprising reacting pyrithione or a water-soluble salt of pyrithione and a water-soluble polyvalent metal salt selected from the group consisting of zinc salts, tin salts, cadmium salts, bismuth salts, copper salts, zirconium salts, magnesium salts, aluminum salts, nitrate salts, acetate salts, sulfate salts, halide salts, and combinations thereof, in a pressurized turbulent flow reactor that generates pulverizing forces, said reaction producing said submicron sized particles of pyrithione salt wherein said water-soluble salt of pyrithione is selected from the group consisting of sodium pyrithione, potassium pyrithione, lithium pyrithione, ammonium pyrithione, and combinations thereof.

3. The method of claim 2, wherein said divalent salt is selected from the group consisting of zinc sulfate, zinc chloride, zinc acetate, copper chloride, and combinations thereof.

4. The method of claim 1, wherein said reacting step further comprises adding a dispersant selected from the group consisting of sodium salts of polymerized alkyl naphthalene sulfonic acids, and combinations thereof.

5. The method of claim 4, wherein said dispersant is present in a blend with a surfactant.

6. The method of claim 1, wherein the ratio of said pyrithione or water-soluble salt of pyrithione to said water-soluble polyvalent metal salt is in the range from about 1:2 to about 1:8.

7. The method of claim 1, further comprising the step of isolating said submicron particles of pyrithione salt.

8. The method of claim 1, wherein the pressure maintained in said pressurized turbulent flow reactor is greater than 1000 psi.

9. The method of claim 1, wherein said reacting step takes place at a temperature of from about 0° C. and about 23° C.

10. The method of claim 1, wherein said pulverizing forces are selected from the group consisting of shear forces, impact forces, cavitation forces, sonication forces, and combinations thereof.

11. The method of claim 1, wherein said submicron-sized particles of pyrithione salt have sizes in the range of about 0.03 μm to about 0.95 μm.

12. The method of claim 11, wherein said submicron-sized particles of pyrithione salt have sizes in the range of about 0.04 μm to about 0.88 μm.

13. The method of claim 12, wherein said submicron-sized particles of pyrithione salt have sizes in the range of about 0.30 μm to about 0.45 μm.

14. A shampoo or skin-care composition comprising a base fluid and submicron particles of pyrithione salts made by the method of claim 1.

15. The composition of claim 14, wherein said base fluid is selected from the group consisting of surfactants, dispersants and combinations thereof.

16. A method for producing submicron-sized particles of zinc pyrithione, comprising reacting a pyrithione or a water-soluble salt of pyrithione and a water-soluble zinc salt selected from the group consisting of zinc sulfate, zinc chloride, zinc acetate, and combinations thereof, in a turbulent flow reactor generating pulverizing forces, said turbulent flow reactor maintained at a pressure of from about 18,000 psi to about 23,000 psi and a temperature of from about 0° C. to about 23° C., said reaction producing submicron-sized particles of zinc pyrithione.

17. The method of claim 16, wherein said water-soluble salt of pyrithione is selected from the group consisting of sodium pyrithione, potassium pyrithione, lithium pyrithione, ammonium pyrithione, and combinations thereof.

18. The method of claim 16, wherein said reacting step further comprises adding a dispersant selected from the group consisting of sodium salts of polymerized alkyl naphthalene sulfonic acids, and combinations thereof.

19. The method of claim 18, wherein said dispersant is present in a blend with a surfactant.

20. The method of claim 16, wherein the ratio of said pyrithione or a water-soluble salt of pyrithione to a water-soluble polyvalent metal salt is in the range from about 1:2 to about 1:8.

21. The method of claim 16, further comprising the step of isolating said submicron particles of zinc pyrithione.

22. The method of claim 16, wherein said pulverizing forces are selected from the group consisting of shear forces, impact forces, cavitation forces, sonication forces, and combinations thereof.

23. The method of claim 16, wherein said submicron particles of zinc pyrithione have sizes in the range of about 0.03 μm to about 0.95 μm.

24. The method of claim 23, wherein said submicron particles of zinc pyrithione have sizes in the range of about 0.04 μm to about 0.88 μm.

25. The method of claim 24, wherein said submicron particles of zinc pyrithione have sizes in the range of about 0.30 μm to about 0.45 μm.

26. A shampoo or skin-care composition, comprising a base fluid and submicron-sized particles of zinc pyrithione made by the method of claim 16.

27. The composition of claim 26, wherein said base fluid is selected from the group consisting of surfactants, dispersants, and combinations thereof.

* * * * *